US005616473A

United States Patent [19]
Farrell et al.

[11] Patent Number: 5,616,473
[45] Date of Patent: Apr. 1, 1997

[54] CLONING AND EXPRESSION OF LIGNINASES

[75] Inventors: Roberta L. Farrell, Danvers; Paul Gelep, Boston, both of Mass.; Algis Anilionis, Pittsford, N.Y.; Kashayar Javaherian, Lexington, Mass.; Theodore E. Maione, Concord, Mass.; James Rusche, Worcester, Mass.; Bruce A. Sadownick, Waltham, Mass.; Jennifer A. Jackson, Reading, Mass.

[73] Assignee: Clariant Finance (BVI) Limited, Tortola, Virgin Islands (Br.)

[21] Appl. No.: 287,022

[22] Filed: Aug. 8, 1994

Related U.S. Application Data

[63] Continuation of Ser. No. 132,618, Oct. 6, 1993, abandoned, which is a continuation of Ser. No. 7,442, Jan. 22, 1993, abandoned, which is a continuation of Ser. No. 838,641, Feb. 20, 1992, abandoned, which is a continuation of Ser. No. 578,964, Sep. 26, 1990, abandoned, which is a continuation of Ser. No. 48,202, May 11, 1987, abandoned, which is a continuation-in-part of Ser. No. 906,853, Sep. 12, 1986, abandoned.

[51] Int. Cl.$^6$ .......................... C07H 21/04; C12N 15/31; C12N 15/52; C12N 15/81
[52] U.S. Cl. .................. 435/69.1; 435/172.1; 435/320.1; 536/23.1; 536/23.2; 536/23.7
[58] Field of Search .............................. 435/69.1, 320.1, 435/172.1, 172.3; 536/23.1, 23.2, 23.7

[56] References Cited

PUBLICATIONS

Tren et al. "Lignin–degrading Enzyme from *Phanerochaete chrysosporium*: Purfication, Characterization and Catalytic Properties of a a unique $H_2O_2$–Requiring Oxygenase", PNAS, vol. 81, pp. 2280–2284, 1984.

Zhang et al. "Identification of a CDNA Clones for Ligninase from *Phanerochaete chrysosporium* Using Synthetic Oligonucleotide Probes", Biochem. Biophys. Res. Comm., vol. 137, No. 2, pp. 649–656, Jun. 13, 1986.

Alberts et al. "Molecular Biology of the Cell", Garland Publishing Co., Inc., New York (1983), pp. 184–193.

Watson et al. "Recombinant DNA: A Short Course", W.H. Freeman and Co., New York (1983) pp. 50–90.

Haylock et al. "Molecular Genetics of *Phanerochaete chrysosporium*" Confernece of Lignocellulose Biodegradtion, Abstract, 1984, pp. 365–366.

R. Haylock, et al. "Isolation of mRNA from P. chrysosporium and its In Vitro Translation". J. Microbiol. Methods, 1985, 4(3–4), pp. 155–162.

U. Raeder, etal. "Rapid Preparation of DNA from Filamentous Fungi", Letters in Applied Microbiol. 1985, 1(1), pp. 17–20.

M. Tien, et al. "Cloning and Sequencing of acDNA for a Ligninase from *P. chrysosporium*", Nature. vol. 326, 2 Apr. 1987, pp. 520–523.

Corrigendum for the above (Reference AU), Nature vol. 328, 20 Aug. 1987, p. 742.

*Primary Examiner*—David Guzo
*Attorney, Agent, or Firm*—Robert S. Honor; Carl W. Battle; Michael P. Morris

[57] ABSTRACT

The gene encoding the ligninase rLDM™ 6 has been cloned and expressed. The ligninases produced via the processes disclosed herein are useful to degrade or modify lignin in pulp operations.

16 Claims, 7 Drawing Sheets rLDM™ 6  1  2  3   4   5   6   7   8   9  10  11  12  13      16  17
         Ala Thr _ Ser Asn Gly Lys Thr Val Gly Asp Ala Ser _ _ Ala Trp

FIGURE 2

Mature rLDM™ 6 N-terminal sequence rLDM™6  1   2   3   4   5   6   7   8   9  10  11  12  13          17
        Ala Thr  _  Ser Asn Gly Lys Thr Val Gly Asp Ala Ser  _   _   _  Trp 3-2     1   2   3   4   5   6   7   8   9  10  11  12  13  14  15  16  17
        Ala Thr Cys Ser Asn Gly Lys Thr Val Gly Asp Ala Ser Cys Cys Ala Trp

FIGURE 3

Alignment of Mature rLDM™6 N-terminal sequence
with Early Sequence From Clone 3-2

TIME COURSE OF ACTIVITY RECOVERY – RECONSTITUTED rLDM™ 6

PHYSICAL MAP OF PLN106

CmR = chloramphenicol resistance gene

ApR = ampicillin resistance gene ori = origin of replication

CONSTRUCTION OF pLn106

Schematic of pREV2.2 and of Multiple Cloning Site

CLONING AND EXPRESSION OF LIGNINASES

This is a continuation of application Ser. No. 08/132,618, filed Oct. 6, 1993, now abandoned, which in turn is a continuation of application Ser. No. 08/007,442, filed Jan. 22, 1993, which in turn is a continuation of application Ser. No. 07/838,641, filed Feb. 20, 1992 which in turn is a continuation of application Ser. No. 07/578,964, filed Sep. 26, 1990, which in turn is a continuation division of application Ser. No. 07/048,202, filed May 11, 1987, which in turn is a continuation-in-part of application Ser. No. 06/906,853, filed Sep. 12, 1986, the latter five of which are now abandoned.

BACKGROUND OF THE INVENTION

The field of this invention is lignin and lignin modifying and degrading enzymes. Lignin is a complex polymer formed by free radical polymerization of substituted cinnamyl alcohol precursors. Lignin constitutes 15–35% of dry wood weight. During pulping processes, cellulosic fibers must be liberated from their encasing lignin matrix so that they can associate with one another, yielding strength in the final product. This polymer separation can be accomplished by removal of lignin as in chemical pulps, or by maintaining the lignin as in high yield mechanical pulps. During the bleaching process, lignin is removed and the resulting pulp is brightened.

Lignin is highly resistant to biological attack. No organism has been demonstrated to grow on lignin as the sole carbon source. The complex lignin polymer, however, is completely degraded by pure cultures of various higher order fungi. The most extensive physiological investigations of lignin biodegradation by white-rot fungi have been conducted with a single member of the family Corticraceae, *Phanerochaete chrysosporium* Burds.

Under defined laboratory conditions, fungal lignin degradation is not observed during approximately the first 3 days of culture. Subsequently, the culture becomes starved for carbon or nitrogen, and lignin degradation is first observed at day 4 or 5 of culture and is maximal at 6 days. The induction of lignin degradation in response to carbon and nitrogen starvation indicates that fungal lignin metabolism is a secondary metabolic event (Keyser, P., Kirk, T. K. and Zeikus, J. G. [1978] J. Bacteriol. 135:790–797).

Fungal lignin degradation currently is commercially impractical for several reasons. The rate of lignin degradation is unacceptably slow since ligninolytic activity is induced only as a result of secondary metabolism. Therefore, a period of initial growth followed by starvation is required. Furthermore, fungi metabolize cellulosic fibers as their primary food source, resulting in reduced pulp yield and an inferior pulp product.

Tien and Kirk have disclosed a preparation capable of oxidatively cleaving $C_\alpha$–$C_\alpha$ bonds in lignin model compounds and oxidatively converting veratryl alcohol to veratrylaldehyde (Tien, M. and Kirk, T. K. [1984] Proc. Natl. Acad. Sci. 81: 2280–2284). This preparation displays on an SDS-polyacrylamide gel predominantly one protein with an apparent molecular weight of 42 kD and several minor bands. Thus the preparation is a mixture of proteins. Subsequent to the publication of this paper, several scientific papers were published disclosing an inability to isolate the major protein from the mixture. These articles are as follows: Huynh, V-B and Crawford, R. L. (1985) FEMS Microbiology Letters 28:119–123; Leisola, M. et al. (1985) Lignin Biodegradation Workshop; and Gold, M. H. et al. (1985) Lignin Biodegradation Workshop.

These attempted protein isolations have been done either by ion-exchange chromatography or by size exclusion ion exchange column chromatography. The fractions containing the indicated component have been analyzed by isoelectric focusing or SDS-polyacrylamide gel electrophoresis, and have been shown to contain more than one protein species.

In pending U.S. application Ser. No. 845,655, filed on Mar. 28, 1986, now U.S. Pat. No. 4,687,741, there is disclosed and claimed, inter alia, an enzyme preparation designated rLDM™ 6. (rLDM™ is the trademark of the Repligen Corporation, Cambridge, Mass., for lignin degrading and modifying enzymes.) This preparation is substantially pure and hence also substantially free of other rLDM™ and degrading native proteases. It is also substantially free of native proteins having different activities which are present in the Tien and Kirk mixture, supra. Advantageously, this rLDM™ 6 preparation possesses desirable properties for use in pulping wood and treating effluent which the Tien and Kirk preparation does not have. Specifically, the Tien and Kirk mixture has a lower specific activity than rLDM™ 6. The rLDM™ have been characterized by the critical property of being able to catalyze the oxidation of veratryl alcohol to veratrylaldehyde (ligninase activity), and the following physical parameters:

(1) molecular weight as determined by SDS-PAGE;
(2) amino acid composition;
(3) heme content;
(4) homology by antibody reactivity;
(5) specificity of activity against lignin model substrates; and
(6) elution from a FPLC column at specified sodium acetate molarities.

Though the preparation of rLDM™ 6 can be carried out as described in Ser. No. 845,655, now U.S. Pat. No. 4,687,741, the disclosure of which is incorporated herein by reference, it could be expected that more efficient production of rLDM™ 6 would be realized if DNA encoding rLDM™ 6 could be cloned and expressed in a suitable host. The task of such a successful cloning and expression is formidable. Further, it is nonobvious (unpredictable) whether there can be expression of activity of a *P. chrysosporium* gene in a heterologous host since this has never been achieved previously. Still further, the prior art provides no suggestions as to how such a cloning and expression invention could be achieved. The applicants in this application for patent have overcome these prior art barriers by successfully cloning and expressing rLDM™ 6.

BRIEF SUMMARY OF THE INVENTION

Disclosed and claimed is the cloning and expression of rLDM™ 6. This recombinantly produced protein, when reconstituted with heme, exhibits the same ligninase activity as the purified natural LDM™ 6. The enzyme produced by recombinant DNA techniques is indicated to degrade/modify lignin without, advantageously, attacking cellulose or hemicellulose. Like the natural enzyme, the rLDM™ 6 enzyme is immediately active and requires no metabolic induction as is necessitated by use of natural fungal isolates.

Specifically disclosed are novel plasmids, e.g., pLn106, comprising a novel nucleotide sequence coding for the amino acid sequence of rLDM™ 6. The DNA sequence of this novel oligonucleotide, and the deduced amino acid sequence is shown in Table 1. Plasmid pLn106 was constructed as shown in FIG. 6.

The disclosed essentially pure nucleotide sequences enable persons in the art, for the first time, to obtain cloned nucleotide sequences coding for rLDM™ 6 and sub-fragments thereof.

Having the above essentially pure nucleotide sequences, those skilled in the art can readily appreciate the identity of other equivalent nucleotide sequences coding for rLDM™ 6 ligninases. Thus, the scope of the subject invention includes not only the specific nucleotide sequences disclosed herein, but also all equivalent nucleotide sequences coding for molecules with substantially the same rLDM™ 6 ligninase activity. The term "equivalent" is being used in its ordinary patent usage here as denoting a nucleotide sequence which performs substantially as the nucleotide sequences identified herein to produce molecules with substantially the same rLDM™ 6 ligninase activity. Within this definition are subfragments and ligninase protein expressed from DNA sequences which hybridize to the discovered native DNA sequence for mature LDM™ 6 protein. The rLDM™ 6 product of the subject invention, and ligninase subfragments and the modification thereof, can be used in the same manner to degrade or modify lignin. Further, the rLDM™ 6 recombinant protein, when constituted. with the oxidized form of protoheme IX, has activity on kraft lignin, milled wood lignin and lignin model compounds. It is indicated that the recombinant rLDM™ 6 when constituted with the oxidized form of protoheme IX has activity on unbleached kraft pulp and mechanically-derived pulps.

DESCRIPTION OF THE DRAWINGS

FIG. 2: MATURE rLDM™ 6 N-Terminal Sequence

FIG. 3: Alignment of Mature rLDM™ 6 N-Terminal Sequence with Early Sequence from Clone 3-2

CULTURE DEPOSITS

Figure 1:
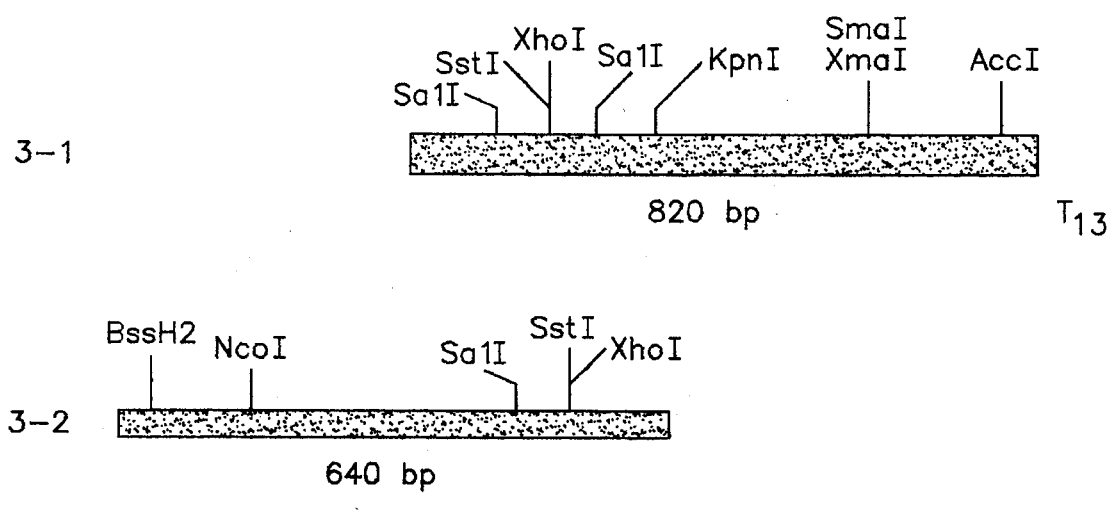
FIG. 1: Restriction Site Maps and Estimated Sizes of Clones 3-1 and 3-2

The following deposits of cultures disclosed inthis application have been made in the Agricultural Research Culture Collection (NRRL), Northern Regional Research Center, U.S. Department of Agriculture, 1815 North University Street, Peoria, Ill. 61604, USA.

| Culture | Repository No. | Deposit Date |
| --- | --- | --- |
| E. coli(pLn105) | NRRL B-18156 | Dec. 31, 1986 |
| E. coli(pLn106) | NRRL B-18157 | Dec. 31, 1986 |
| E. coli(pBSR3) | NRRL B-18068 | May 1, 1986 |
| E. coli K12 JM105 | NRRL B-18067 | May 1, 1986 |
| E. coli(pREV2.2) | NRRL B-18091 | July 30, 1986 |
| E. coli(pLn1001) | NRRL Y-18163 | Jan. 14, 1987 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

DETAILED DISCLOSURE OF THE INVENTION

Cloning of the DNA sequence coding for rLDM™ 6 was initiated by preparing sufficient quantities of RNA from a fermentation of *Phanerochaete Chrysosporium.* Enhanced quantities of RNA were prepared from a UV induced mutant of ATCC 24725, designated SC26, NRRL 15978.

After copying the mRNA with reverse transcriptase, a gene bank comprising DNA sequences coding for genes involved in secondary metabolism including lignin-modifying or -degrading enzymes was constructed.

Antibody reactive against rLDM™ 6 was used to probe the bank. Cross-reactive clones were detected.

Phage DNA was prepared from isolates of the clones, using standard procedures. This DNA was then inserted into suitable vectors for transformation into competent hosts.

Plasmid pBSR3, constructed as described in Example 6a, infra, is carried in *E. coli* JM105, which is not an amber suppressed host. Amber suppressed hosts are known and available in the art. For example, such a host is *E. coli* JM103, NRRL B-18150.

Figure 6:
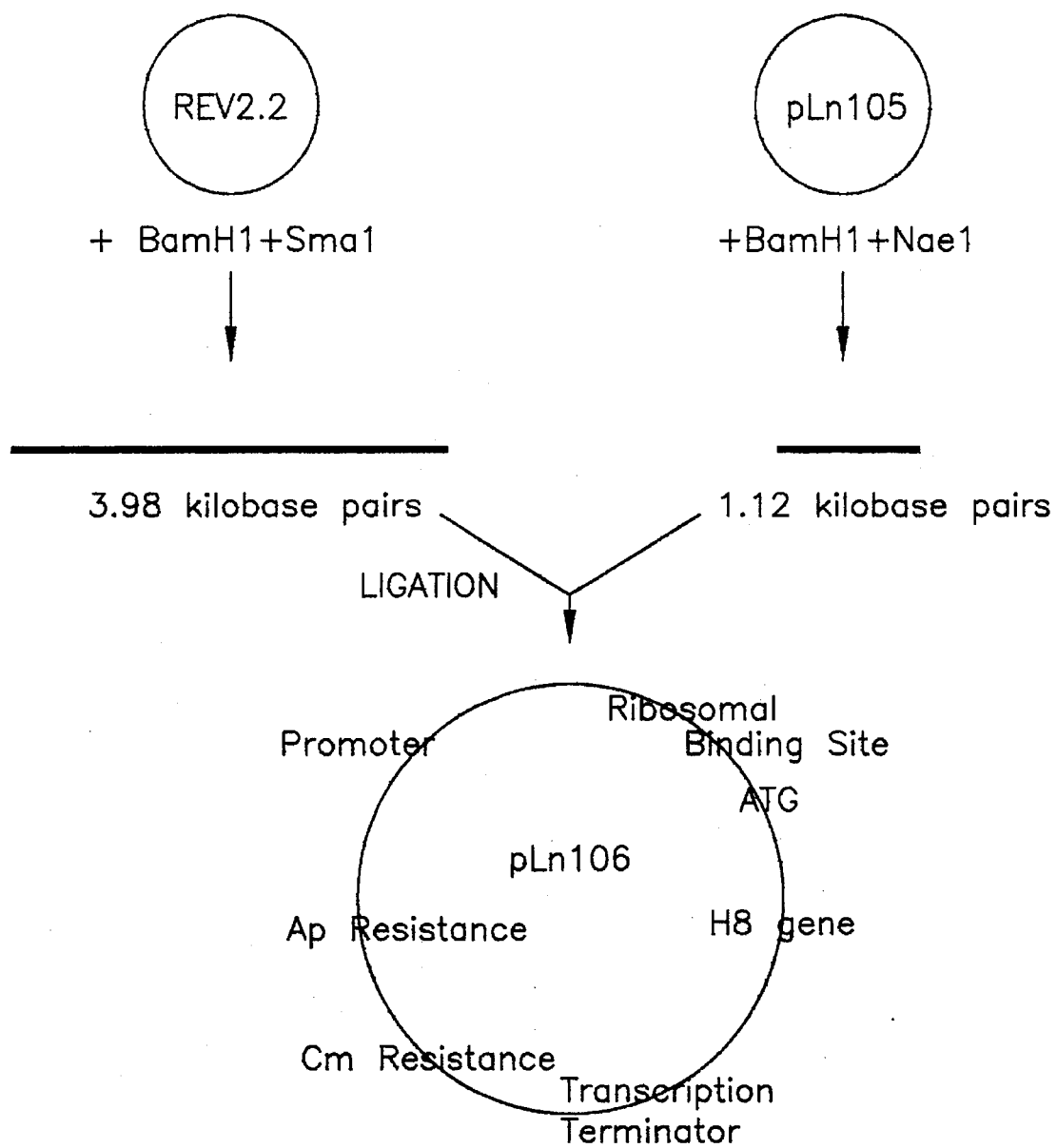
FIG. 6: Schematic of pLn106 Construction
Figure 7:
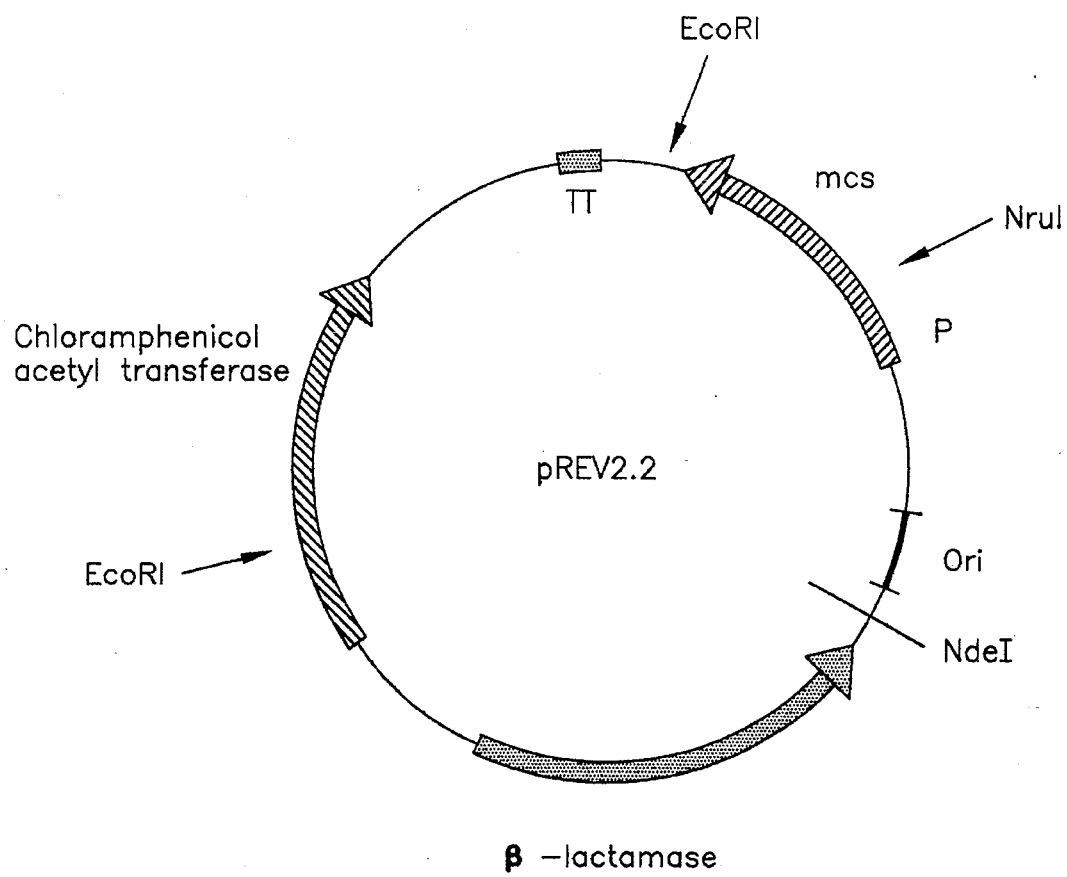
FIG. 7: Schematic of pREV2.2 and of Multiple Cloning Site
Figure 7:
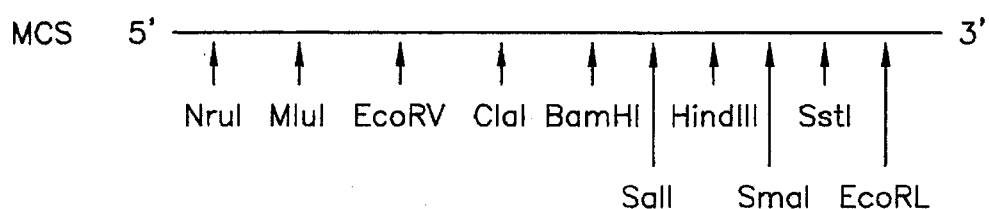

A detailed disclosure of the construction of pLn105 is given in Example 12. Expression vector plasmid pREV2.2, NRRL B-18091, was used to construct plasmid DLn 105 and pLn106. Construction of pLn106 is shown in FIG. 6. A schematic of pREV2.2 is shown in FIG. 7 of the drawings. A detailed disclosure of the construction of pLn106 is given in Example 13.

Ligninase protein which may be produced by recombinant means in accordance with the invention includes not only the mature LDM™ 6 protein but also various modifications thereof having ligninase activity. Proteins comprising the mature LDM™ 6 sequence extended by one or more amino acids at its normal N-terminus have been produced as demonstrated. Protein comprising said mature sequence extended at its normal C-terminus by additional amino acids may also be produced as indicated herein by causing the expression of expression plasmids in an amber host. A variety of other modifications either of a natural origin or constructed by known procedures are also included within the scope of the invention. It can be recognized, for example, that naturally occurring alleles of the herein cloned protein will most probably exist. Such alleles, representing one or more modification in the DNA sequence discovered as coding for LDM™ 6, may code for the same LDM™ 6 protein or for a modified protein having the same ligninase reactivity. Such alleles may be obtained, for example, from natural sources by probing suitable cDNA or genomic DNA banks derived from *P. chrysosporium* or similar wood-degrading fungi with one or more appropriate lengths of tagged DNA excised from the DNA coding for the mature sequence of LDM™ 6 as disclosed herein, having at least about 20 nucleotides to about 300 nucleotides.

Fragments of allelle cDNA and/or genomic DNA isolated as a result of such probing, may be combined with such other cDNA and/or genomic DNA as required to form the desired full length coding sequence in the same general manner that the LDM™ 6 fragments were combined in the cloning of LDM™ 6 as disclosed herein. Modified sequences also may be prepared directly from the cDNA or genomic DNA sequence disclosed herein as coding for LDM™ 6 by employing established known techniques such as site specific mutagenesis, loop-out procedures and other known methods for substituting nucleotides. Hence, in a broader aspect of the invention, nucleotide sequences provided in accordance with this invention include those cDNA and/or genomic DNA sequences which code for protein having ligninase activity and which hybridize to the sequence coding for mature LDM™ 6 protein as disclosed in Table 1 hereof under stringent hybridizing conditions (e.g., 60° C. in 2.5× saline citrate buffer). However, as will also be appreciated, a cDNA and/or genomic DNA coding sequence of native origin may be substantially modified or reconstructed to produce very dissimilar DNA sequences coding for the same or similar protein, typically for purposes of enhancing expression in heterologous or non-native host systems. Hence, in another aspect, the invention provides in general cDNA and/or genomic DNA sequences coding for LDM™ 6 and modified LDM™ 6 proteins which have the ligninase activity characteristic of LDM™ 6.

Following are examples which illustrate procedures for practicing the invention. These examples should not be construed as limiting. All percentages are by weight and all solvent mixture proportions are by volume unless otherwise noted.

EXAMPLE 1—Culture Source of RNA

*P. chrysosporium* NRRL 15978 was grown on a nitrogen-limited trace element medium supplemented with glucose and buffered at pH 4.5

Ligninase activity in the fermentation medium was measured periodically by standard means determining the rate of oxidation of veratryl alcohol to veratrylaldehyde.

Isolation and purification of the novel rLDM™ from the extracellular fluid in the fermentation was accomplished by ultrafiltration and FPLC using an anion exchange column.

(A) Growth conditions

Cultures of NRRL 15978 were grown in 125 ml Erlenmeyer flasks as stationary growths, in a disk fermenter, in 1 liter or 2 liter shaking Erlenmeyer flasks, or in a 20 liter fermenter. The first 2 types of cultures were grown in the following medium, designated nitrogen-limited BIII/glucose medium:

$1.08 \times 10^{-3}$M ammonium tartrate, $1.47 \times 10^{-2}$ M $KH_2PO_4$, $2.03 \times 10$M $MgSO_4 \cdot 7H_2O$, $6.8 \times 10^{-4}$ M $CaCl_2 \cdot 2H_2O$, $2.96 \times 10^{-6}$M thiamine.HCl and 10 ml·$L^{-1}$ of a trace element solution. The trace element solution contains $7.8 \times 10^{-3}$M nitriloacetic acid, $1.2 \times 10^{-2}$M $MgSO_4 \cdot 7H_2O$, $1.7 \times 10^{-2}$M NaCl, $3.59 \times 10^{-4}$M $FeSO_4 \cdot 7H_2O$, $7.75 \times 10^{-4}$ M $CoCl_2$, $9.0 \times 10^{-4}$M $CaCl_2$, $3.48 \times 10^{-4}$M $ZnSO_4 \cdot 7H_2O$, $4 \times 10^{-5}$ M $CuSO_4 \cdot 5H_2O$, $2.1 \times 10^{-5}$ M $AlK(SO_4)_2 \cdot 12H_2O$, $1.6 \times 10^{-4}$M $H_3BO_3$, $4.1 \times 10^{-5}$M $NaMoO_4 \cdot 2H_2O$ and $2.9 \times 10^{-3}$M $MnSO_4 \cdot H_2O$.

The medium was supplemented with 10% (by wt/liter) of glucose and buffered with 10.8 mM ammonium tartrate, pH 4.5 with 7× trace metals (basal level +6×) and 0.04M veratryl alcohol. The shake flask cultures and 20 liter fermenter were in the same medium but with the addition of 0.1% Tween 80.

The 125 ml stationary Erlenmeyer flasks containing 0 ml of culture medium were inoculated with 0.5 ml of the mycelial inoculum and flushed on days 0, 3, and 6 with $O_2$. Inoculation was by addition of 100 ml of the mycelial inoculum. Within 1 day after inoculation, the scored disks were covered by a thin mycelial mat. The rotating biological contactors (RBCs) were flushed continuously through ports in the cover with $O_2$ at 100 ml per min.

The 1 liter or 2 liter shaking Erlenmeyer flasks, containing 300 or 600 ml culture medium, respectively, were inoculated with 50 or 100 ml of the mycelial inoculum. The flasks were shaken in a New Brunswick (New Brunswick Scientific, Edison, N.J.) incubator at 250 rpm at 39° C. Cultures were flushed on days 0, 2, 4 and 6 with $O_2$.

The 20 liter Virtis fermenter (Series 43) (The VirTis Co., Inc., Gardiner, N.Y.) containing 10–14 liters of culture medium, was inoculated with the non-homogenized fungus from a 7 day old ligninase positive 1 liter (300 ml) shaking Erlenmeyer flask. The impeller blades of the fermenter rotated at 300 rpm. Oxygen was introduced by diffusion through approximately 50 feet of Corning silastic 0.058 inch medical tubing (Corning Glass Works, Corning, N.Y.). Oxygen flow equalled 300 ml/min.

(B) Ligninase assay

Ligninase activity in the flasks or RBCs was measured periodically by determining the rate of oxidation of veratryl alcohol to veratrylaldehyde (abbreviated as VAO for veratryl alcohol oxidation). Reaction mixtures contained 275 μl of extracellular fluid, or approximately 0.5 μg of purified enzyme, 2 mM veratryl alcohol, 0.4 mM $H_2O_2$ and either 20 or 100 mM sodium tartrate, pH 2.9 in a final volume of 0.5 ml. The reactions were started by $H_2O_2$ addition and were monitored at 310 nm. Protein was determined according to Bradford, M. M., (1976) Anal. Biochem. 72: 248–254, using bovine serum albumin (Sigma Chemical Co., St. Louis, Mo.) as standard or by using the 409 nm absorbance of a protein solution and calculating protein amount from the extinction coefficient of ligninase.

(C) Purification of ligninases

The extracellular fluid, prepared as described above, was prefiltered through a Millipore (Millipore Corporation, Bedford, Mass.) 0.45 μm filter and concentrated 20-fold by ultrafiltration through an Amicon (Danvers, Mass.) YM10 filter (henceforth, this concentrate is called Ligninolytic Mixture, LM™), dialyzed against 10 mM sodium acetate, pH 6.0, and filtered through 0.45 μm filters (Acrodisc Low Protein Binding, Gelman, Ann Arbor, Mich.). HPLC (high performance liquid chromatography) was performed with the filtered LM™ on a Gilson (Gilson Co., Inc., Worthington, Ohio) system equipped with an LDC/Milton Roy (Milton Roy Co., Rochester, N.Y.) fixed 410 wavelength detector as well as a Gilson variable wavelength detector using a Pharmacia (Piscataway, N.J.) FPLC Mono Q anion exchange column to purify the ligninases according to their elution from the column. The mobile phase consisted of a gradient from 10 mM to 1M sodium acetate, pH 6.0, and in typical preparations was applied over a 40 min period at a flow rate of 2 ml per min with constant monitoring at 410 nm and 280 nm. Each ligninase of interest eluted at a unique sodium acetate molarity from the column (Kirk et al. [1986] Enzyme Microb. Technol. 8:27–32).

(D) Polyacrylamide gel electrophoresis (PAGE)

The ligninases produced by *P. chrysosporium*, NRRL 15978, were analyzed by SDS-polyacrylamide slab gel electrophoresis according to Laemmli, U. K. (1970) Nature 227:680–685. Native slab gels were run according to the procedures of Ornstein, L. (1964) Ann. N.Y. Acad. Sci. 121:321–349; and Davis, B. J. (1964) Ann. N.Y. Acad. Sci. 121:404–427. After electrophoretic separation, the proteins were visualized by coomassie blue staining, or Western blot analysis using standard procedures.

EXAMPLE 2—RNA Preparation

Total RNA was prepared from veratryl alcohol oxidizing fermentation broths of *P. chrysosporium*. PolyA$^+$ mRNA was purified from total RNA by oligodT-cellulose chromatography using standard well-known procedures.

EXAMPLE 3—cDNA Preparation

Ten micrograms of polyA$^+$ mRNA, as obtained in Example 2, was primed with oligodT$_{12-18}$ and copied with reverse transcriptase essentially as described by Gubler and Hoffman (Gubler, U. and Hoffman, B. J. [1983] Gene 25:263–269).

The cDNA was cloned into the well-known and commercially-available vector lambda-gt11 (Young, R. A. and Davis, R. W. [1983] Proc. Natl. Acad. Sci. USA 80:1194–1198; available from Vector Cloning Systems, San Diego, Calif.). Double stranded cDNA was methylated with EcoRI methylase enzyme (New England Biolabs, Beverly, Mass.) and S-adenosyl-methionine as recommended by the supplier and ligated with a mixture of three EcoRI linkers (GGAATTCC, CGGAATTCCG and CCGGAATTCCGG). These linkers insure that fusions in all three translational reading frames can be obtained.

The EcoRI linked cDNA was cleaved with EcoRI endonucleases and a fraction from 600 to 2,000 base pairs was isolated from a 1% agarose gel. This purified EcoRI cleaved cDNA was ligated with EcoRI cut, phosphatase-treated lambda-gt11 DNA, packed into phage and used to infect *E. coli* Y1088, ATCC 37195.

All restriction endonucleases used herein were purchased from Bethesda Research Laboratories, Gaithersburg, Md. or New England Biolabs, Beverly, Mass., and were used according to the directions of the supplier.

EXAMPLE 4—Antibody Screening

Rabbit anti-rLDM™ antibody reactive against HPLC-purified *P. chrysosporium* LDM™ 6 was used to probe the bank derived from the 600–2,000 bp cDNA. Cross-reactive clones were detected.

Phage DNA was prepared from isolates of each of the cross-reactive clones by standard procedures (see, for example, Maniatis, T. et al. [1982] Molecular Cloning: A Laboratory Manual. Cold Spring Harbor Laboratory, N.Y.) and digested with EcoRI to reveal the size of the cDNA insert. The insert size of the clone designated 3-1 as estimated is 820 bp. Four other clones also contained similar inserts of approximately 650 bp, of which clone 3-2 is representative.

FIG. 1 shows the restriction maps derived of clones 3-1 and 3-2. Clone 3-1 contains the expected oligodT tract (used to prime the cDNA synthesis) contiguous with an EcoRI linker sequence.

EXAMPLE 5—N-Terminal Characterization of rLDM™ 6 rLDM™ 6 was purified from the extracellular growth medium of *P. chrysosporium* from mutant SC26 by ion-exchange HPLC as described by Kirk et al. (Kirk, T. K., Croan, S., Tien, M., Murtagh, K. E. and Farrell, R. L. [1986] Enzyme Microb. Technol. 8:27–32). This isolate was subjected to N-terminal amino acid analysis by HPLC (Hunkapiller, M. and Hood, L. [1983] Methods in Enzymol. 91: 227,486.) The N-terminal results are given in FIG. 2.

Cysteine is not detected in this system and thus the third, 14th and 15th amino acids were registered as blanks.

EXAMPLE 6—Characterization of the Ligninase rLDM™ 6 Gene Sequence

Analysis of DNA sequence information from the presumed 5' end of the clone 3-2 showed a sequence consistent with the experimentally determined mature rLDM™ 6 N-terminus as given in FIG. 3. A full length cDNA clone was reconstructed by splicing together clones 3-2 and 3-1 at their common SstI sites, yielding an EcoRI-SstI-EcoRI fragment of approximately 1280 bp. This EcoRI-Sst-EcoRI fragment was cloned by ligating the fragment with the DNA obtained on linearizing the plasmid pREV2.2 with the restriction endonuclease EcoRI, transforming *E. coli* JM105 (NRRL B-18068) with the resulting vector and culturing the transformed cells.

This shows a very non-standard cloning procedure by independently finding the predicted N-terminal and C-terminal halves of the protein, respectively.

The total DNA sequence of this rLDM 6 clone has been determined and is given in Table 1. When this DNA sequence is appropriately inserted into a suitable expression vector, e.g., a plasmid, and the vector is used to transform a non-amber suppressed bacterium, e.g., *E. coli* JM105, the host bacterium, upon cultivation, expresses a protein whose amino acid sequence, as found in Table 1, extends from the 1-position Ala to a C-terminus of the amino acid sequence at the Ala (position 344) just prior to the stop signal at location 345. When an amber suppressed host such as *E. coli* JM103 was transformed by the vector, the C-terminus of the amino acid sequence shown in Table 1 is Gly at amino acid position 361, which is located prior to the stronger stop signal at location 362. The amino acid sequence of the mature rLDM™ 6-apo-protein predicted from the cDNA sequence is 344 residues, extending from the 1-position Ala to the 344-position Ala.

EXAMPLE 6a—Preparation of Expression Plasmid pBSR3

Since a portion of the codon for the Ala at the beginning of the mature rLDM™ 6 sequence includes a portion of a BssHII site (GCGCGC), the balance of said site preceding the Ala codon and including all of the CGC codon for Arg at a minus 1-position, a BssHII-SstI-EcoRI DNA fragment containing all of the coding strand information for rLDM™ 6 was excised from the cloning plasmid (Example 6) by first cutting the same with the restriction endonuclease BssHII and filling in the resulting 5' overhang by treatment with the Klenow fragment of DNA polymerase, hence fully reestablishing the DNA for encoding the amino acids Ala and Arg. The resulting linearized and treated plasmid DNA was then digested with the endonuclease EcoRI to free the desired fragment. This fragment after gel isolation was used to form the expression plasmid pBSR3 as a protein fusion system with the plasmid pREV2.2 shown in FIG. 7. As shown in FIG. 7, the plasmid pREV2.2 includes a multiple cloning site (MCS) downstream from a promoter (P). Restriction sites within the multiple cloning site are shown in the linearized MCS segment in FIG. 7. To prepare pBSR3, the plasmid pREV2.2 was digested with the restriction endonucleases EcoRI and EcoRV and the resulting linearized plasmid was ligated with the above-obtained and modified BssHII-SstI-EcoRI fragment by standard ligating procedure. Hence, the sequence coding for the mature protein beginning with GCC in pBSR3 is preceded at its 5' or upstream end by said CGC coding for said Arg, and this in turn is immediately preceded by 87 bp coding for 29 amino acids (contributed by the MCS section ) which, in turn, are immediately preceded by ATG coding for Met. Thus, pBSR3 codes for an amino acid sequence which has the mature sequence of LDM™ 6 preceded at its ordinary N-terminus by a section of 31 amino acids which has a Met as its N-terminus. The expression of pBSR3 in a non-amber host is described in Example 7, below.

EXAMPLE 7—Fermentation and Extraction of Recombinant rLDM™ 6 from *E. coli*

A 20 liter fermenter of *E. coli* (pBSR3), NRRL B-18068, was grown in Modified 2% Yeast Extract Medium without oxygen control for 24–32 hr. The composition of the medium is as follows:

| Ingredient | Amount |
|---|---|
| yeast extract | 20.0 gm/liter |
| casein peptone | 20.0 gm/liter |
| casamino acids | 20.0 gm/liter |
| $KH_2PO_4$ | 2.0 gm/liter |
| $K_2HPO_4$ | 2.0 gm/liter |
| $Na_2HPO_4.7H_2O$ | 2.0 gm/liter |
| chloramphenicol | 100.0 mg/liter |

When aliquots of the harvested cells were analyzed by SDS-PAGE (Laemmli, U.K. [1970] Nature 227:680–685) and visualized with coomassie blue protein stain, a protein band with apparent molecular weight of approximately 41,000 becomes more prominent compared to non-transformed cell controls. That this band represented rLDM™ 6 was verified by Western blot analysis using antibody reactive toward native rLDM™ 6 (Towbin, H., Staehelin, T. and Gordon, J. [1979] Proc. Natl. Acad. Sci. USA 76:4350–4354) which revealed the major immunoreactive protein also to correspond to this molecular weight. This protein is not glycosylated, which distinguishes it from the native (*P. chrysosporium*-produced) protein.

When cells were lysed by sequential lysozyme and bead mill treatment, recombinant rLDM™ 6 was detected only in the pellet fraction. For subsequent fractionation the insoluble material was separated from the soluble proteins under centrifugal conditions appropriate to pellet inclusion bodies (20,000×g, 20 min). It was found that urea or guanidine HCl could solubilize the recombinant rLDM™ 6. In the presence of 10 mM dithiothreitol and 5 mM EDTA the ability of urea to solubilize rLDM™ 6 was enhanced at lower urea concentrations.

EXAMPLE 8—Electrophoresis and Extraction of DNA Fragments

Agarose gel electrophoresis was carried out using a 2X Tris-acetate gel buffer (80 mM Tris-HCl, pH 8.0; 40 mM $NaC_2H_3O_2$; 36 mMNaCl; 2 mM $Na_2$ EDTA) in the gel and 1× buffer for the run. Analytical gels were routinely run as "submarine gels" in a horizontal gel box. DNA bands were visualized by ethidium bromide (EtBr) post-staining (0.5 mg/ml in 1× gel buffer) and use of a UV transilluminator Model TM-36 from UltraViolet Products, Inc., San Gabriel, Calif.

Extraction of DNA from preparative agarose gels was initiated by visualization of the positions of EtBr-stained bands of a single gel lane. Gel slices containing DNA fragments of interest were diced manually and passed through a 20 g needle with 1½–2 volumes DNA gel extraction buffer (0.5M $NH_4C_2H_3O_2$, 10 mM EDTA, 10 mM $Mg(C_2H_3O_2)_2$, 0.1% SDS). An equal volume of phenol saturated with 1 mM $NH_4C_2H_3O_2$, 10 mM EDTA was added and extraction carried out in eppendorf tubes on a rotary shaker at 23° C. overnight. The tubes were then placed on ice for 30 min prior to separation of the aqueous phase by microcentrifugation. Extraction of the aqueous phase with the saturated phenol solution was repeated 3–4 times, followed by chloroform extraction and ethanol precipitation. Routine recovery of DNA fragments smaller than 15 kb was about 40%.

EXAMPLE 9—DNA Sequencing

DNA sequence determination was carried out using procedures described by Maxam and Gilbert (Maxam, A. and Gilbert, W. [1977] Proc. Natl. Acad. Sci. USA 74:560) and Heidecker et al. (Heidecker, G., Messing, J. and Gronenborn, B. [1980] Gene 10:69).

The various methods employed in the preparation of the plasmids and transformation of host organisms are well known in the art. These procedures are all described in Maniatis, T., Fritsch, E. F. and Sambrook, J, (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

EXAMPLE 10—Cloning and Expression of the Nucleotide Sequences Coding for rLDM™ 6

A wide variety of ways are available for introducing the rLDM™ 6 gene into the microorganism host under conditions which allow for stable maintenance and expression of the gene. One can provide for DNA constructs which include the transcriptional and translational regulatory signals for expression of the gene, the gene under their regulatory control and a DNA sequence homologous with a sequence in the host organism, whereby integration will occur, and/or a replication system which is functional in the host, whereby integration or stable maintenance will occur.

The essentially pure nucleotide sequences coding for rLDM™ 6 or for biologically active subfragments of rLDM™ 6, can be ligated into appropriate restriction enzyme sites in an expression cloning vector. If necessary, sites can be added to nucleotide sequences using linker molecules. (See, for example, Norris, K. E. et al. [1979] Gene 7:355–362.) The ligated DNA can then be used to transform competent prokaryotic or eukaryotic cells.

rLDM™ 6 proteins can be expressed in *Saccharomyces cerevisiae* using plasmids containing the inducible galactose promoter from this organism (Broach, J. R., Li, Y., Wu, L. C. and Jayaram, M. in Experimental Manipulation of Gene Expression [1983] p. 83, ed. M. Inouye, Academic Press). These plasmids are called YEp51 and YEp52 (Broach, J. R. et al., 1983, supra) and contain the *E. coli* origin of replication, the gene for β-lactamase, the yeast LEU2 gene, the 2 μm origin of replication and the 2 μm circle REP3 locus. Recombinant gene expression is driven by the yeast GAL10 gene promoter.

Other yeast promoters such as alcohol dehydrogenase (Bennetzen, J. L. and Hall, B. D. [1982] J. Biol. Chem. 257:3018; Ammerer, G. in Methods in Enzymology [1983] Vol. 101, p. 192), phosphoglycerate kinase (Derynck, R., Hitzeman, R. A., Gray, P. W., Goeddel, D. V., in Experimental Manipulation of Gene Expression [1983] p. 247, ed. M. Inouye, Academic Press), triose phosphate isomerase (Alber, T. and Kawasaki, G. [1982] J. Molec. and Applied Genet. 1: 419), or enolase (Innes, M. A. et al. [1985] Science 226: 21) can be used in a similar manner.

The rLDM™ 6 gene can be expressed by the filamentous fungus Aspergillus since this fungus is related to *P. chrysosporium.*

The plasmid pBSR3 is constructed by using the Okayama-Berg cloning system (Okayama, H. and Berg, P. [1983] Molec. and Cell. Biol. 3:280). This vector is designed so that a cDNA, such as that encoding rLDM™ 6, cloned into it can be expressed in simian cells.

When COS cells are transfected with pBSR3 as described in Okayama and Berg (1983) and references therein, synthesis of rLDM™ 6 can be detected immunologically.

Examples of other mammalian cell systems are the vaccinia virus expression system (Moss, B. [1985] Immunology Today 6:243; Chakrabarti, S., Brechling, K., Moss, B. [1985] Molec. and Cell. Biol. 5:3403) and the vectors derived from murine retroviruses (Mulligan R. C. in Experimental Manipulation of Gene Expression [1983] p. 155, ed. M. Inouye, Academic Press).

EXAMPLE 11—Preparation of Expression Plasmid pLn104

Plasmid pBSR3 (Example 6a) was the basis for a standard loop-out experiment to form a modified pBSR3 in which all but one of the codons (the CGC coding for Arg prior to the GCC for the 1-position Ala) in the nucleotide sequence between the initiating ATG and GCC for the 1-position Ala were excised (looped-out). To effect this result, the plasmid pBSR3 was treated with the restriction endonucleases EcoRI and NdeI and the resulting fragment containing the ligninase coding sequence was gel isolated. Another portion of pBSR3 was linearized by treatment with the restriction endonuclease PstI and gel isolated. The two thus isolated segments were then combined with a single stranded 40 base nucleotide designed to effect the desired loop-out and having the sequence TTAATGAGGAGTCCCTTATGCGCGCCACCTGTTCCAACGG. The resulting heteroduplex was treated with DNA polymerase and the resulting system worked upon in a conventional fashion to isolate the desired expression plasmid, designated pLn104. Upon transforming *E. coli* JM105 with pLn104 and culturing the successful transformants, there was expressed a 345 amino acid ligninase protein having the amino acid sequence of mature LDM™ 6 preceded at its normal N-terminal by Arg.

EXAMPLE 12—Construction of expression plasmid pLn105

The plasmid pLn105 was constructed as an operon fusion using the *E. coli* promoter available from pREV2.2 and a linkage downstream therefrom of an oligonucleotide containing a standard non-coding ribosomal binding site followed by an initiator ATG codon which is to be placed immediately prior to the GCC which codes for the 1-position Ala of the mature protein. Hence, pLn105 is designed to code for the amino acid sequence of the mature protein preceded at its N-terminus by Met. More particularly, the plasmid pLn105 was prepared by digestion of the cloning plasmid of Example 6 (formed by simple ligation of EcoRI cut pREV2.2 with the approximately 1280 bp EcoRI-SstI-EcoRI fragment) with the restriction endonuclease BssHII. The resulting linearized plasmid was then digested with S1 nuclease by standard procedures to remove the 5' overhang created by the BssHII digestion. The resulting fragment was then digested with the restriction endonuclease HindIII which cuts in the multiple cloning site section from the plasmid pREV2.2. The resulting large fragment was then ligated by standard ligation procedures with the oligonucleotide

AGCTATAATGAGGAGTCCCTTATGGC
TCGATATTACTCCTCAGGGAATACCG which constituted the above-referred to non-coding ribosomal binding site with attached initiating methionine (ATG) codon and GC portion of the alanine codon (in order to reestablish the GCC coding for the 1-Ala of the mature protein). pLn105 was expressed in *E. coli* host JM103, NRRL B-39403. The N-terminus expresses as methionine-alanine-threonine, etc. as per Table 1.Methionine was not detected in the majority of rLDM™ 6 protein isolated.

EXAMPLE 13—Construction of Plasmid pLn106

Plasmid pLn106 was constructed as indicated in the schematic given in FIG. 6. To summarize from FIG. 6, the plasmid pREV2.2 was digested with the restriction endonucleases BamHI and SmaI which cut in the area of the MCS of REV2.2. The resulting large fragment of about 3,980 bp of DNA was isolated from the digestion fragments. The plasmid pLn105 was digested with the restriction endonucleases BamHI (which cuts in the MCS section originating in pREV2.2) and with NaeI (which cuts just prior to the second stop signal following the sequence for the mature protein as given in Table 1), and the resulting fragment of about 1,118 bp was isolated from the digestion fragments. The above isolated fragments of about 3,980 and 1,118 bp were then ligated together using standard ligation procedures. The resulting plasmid pLn106 contains the genes for chloramphenicol and ampicillin resistance, an origin of replication, *E. coli* promoter, a non-coding ribosomal binding site of the sequence GGAGTCCCTT, the ATG initiating codon and the DNA sequence starting with position 91, GCC . . . to position 1170, GTGGCC . . . , as given in Table 1, said DNA sequence including the sequence encoding rLDM™ 6 starting at said position 91 and extending to position 1122

(ending GGTGCT). The plasmid pLn106 was transformed by standard techniques into *E. coli,* and a 20-liter fermentation was grown by culturing as per Example 7 to induce expression of rLDM™ 6.

Recombinant rLDM™ 6 was isolated from the insoluble pellet fraction, as per Example 7, and purified to 30% by extraction in 4–8M urea, 50 mM sodium acetate, pH 6, 10 mM dithiothreitol (DTT) and resuspended with a POLYTRON (Brinkman Instruments, Westbury, N.Y.) for 30 sec to 3 min. The supernatant extract is separated from the pellet by appropriate centrifugation and the supernatant is run on an anion exchange column, an example of which is DEAE-SEPHAROSE column (Pharmacia, Piscataway, N.J.) in Buffer A (4–8M urea, 50 mM sodium acetate, pH 6, and 5 mM DTT). A gradient of 0 to 0.5–1.0M NaCl is run in Buffer A. Fractions are collected and pooled with rLDM™ 6. The apparent size of rLDM™ 6 produced from this procedure from *E. coli* strain SG20251 (NRRL B-15918) is approximately 39.5 kilodaltons (kd). rLDM™ 6 produced from pLn106 in *E. coli* is not glycosylated, which distinguishes it from the native (*P. chrysosporium*-produced) protein. As described below, isolated rLDM™ 6 which is to be activated/reconstituted can be stored at 4° C. or –20° C. for only 1–2 days before reconstitution for assurance of good reactivity.

The first 8 N-terminal amino acids of such a preparation of rLDM™ 6 have been determined to be Ala Thr Ser Asn Gly Lys Thr, where the blank in this system is generally a cysteine residue. Therefore the initiating ATG codon encoding methionine was not found to be present under these conditions of fermentation and production. The N-terminal methionine may be present in other preparations of rLDM™ 6 depending upon *E. coli* strain, expression level, and method of purification.

When cells were lysed by sequential lysozyme and bead mill treatment, recombinant rLDM™ 6 was detected mainly in the pellet fraction. For subsequent fractionation the insoluble material was separated from the soluble proteins under centrifugal conditions appropriate to pellet inclusion bodies (12,000×g, 5 min). It was found that urea could solubilize rLDM™ 6. Using an extraction solution of 4M urea, 1 mM EDTA, 50 mM Tris-Cl, pH 8.0, 50% of rLDM™ 6 is solubilized from the insoluble fraction. The rest of the rLDM™ 6 produced can be solubilized from the insoluble fraction using 8M urea.

The 4M urea, 1 mM EDTA, 50 mM sodium acetate, pH 6.0 protein extract was reduced with 5 mM dithiothreitol (DTT), diluted with three volumes of Buffer A (4M urea, 5 mM DTT, 50 mM sodium acetate, pH 6.0) and 200 ml applied to a 100 ml DEAE-Sepharose Fast Flow column (Pharmacia). The column was eluted with a linear gradient from 0 to 0.5M NaCl in Buffer A. Twenty five-ml fractions were collected and checked for their immunoreactivity with anti-rLDM™ 6 ligninase antibody. The most strongly immunoreactive fractions were pooled (25 ml) and applied to a sizing column, S-300 (400 ml) Sephacryl (Pharmacia) in 4M urea, 50 mM $KH_2PO_4$, pH7.0, 4 mM DTT. Again immunoreactivity of fractions (10 ml each) from the sizing column was checked and the most strongly reactive were pooled. When examined by SDS-PAGE this pooled fraction appeared to be approximately 20% rLDM™ 6 as judged by scanning the coomassie blue staining pattern. This material was subsequently used for heme reconstitution. Heretofore no successful heme reconstitution of *P. chrysosporium* nor recombinant ligninases has been demonstrated.

Reconstitution Protocol

In order to realize good activity of rLDM™ 6 it is desirable to effect the purification and reconstitution procedures with freshly prepared product. The starting material can be frozen cells but results with frozen lysed cell pellets are not good. After lysis as given in Example 12, the urea extraction mix can stir at room temperature from 0 min to six hr, at which time the extract is centrifuged, from 30 min to 15 hr, depending upon the gravitational force of the centrifugation. The anion exchange column is run immediately and the pooled fractions are put into the reconstitution protocol within 24 hr, unless the pooled rLDM™ 6-containing fractions are held at –20° C., where they can be stored longer before reconstitution, Successful reconstitution, with activation of rLDM™ 6 to at least a specific activity of 26 units veratrylaldehyde produced from veratryl alcohol/min/mg rLDM™ 6, can be achieved with rLDM™ 6 preparations which range in purity from 5–100%. These rLDM™ 6 preparations were made from cells expressing either clone pLn105 or pLn106 (see Examples 12 or 13). These preparations can be in a protein concentration of 0.1 to 1 mg/ml in their elution buffer from the anion exchange column which is typically 0.1 to 0.3M NaCl. The rLDM™ 6 preparation is dialyzed against a 50- to 1,000-fold excess of buffer comprising Tris-Cl, pH about 5 to about 10, about 0.5 to about 20 mM DTT, about 0 to about 30% (v/v) glycerol, 0 to about 2 mM reduced glutathione, and about 0 to about 200 μM oxidized glutathione for about 2 to about 24 hr, at about 4° C. to about 37° C.

Recombinant rLDM™ 6 isolated from the sizing column and judged at 20% purity can be reconstituted with hemin (Sigma). One reconstitution procedure used is as follows: The pooled fraction from the sizing column at 3 mg/ml total protein concentration, with recombinant rLDM™ 6 representing about 20% of total protein, is in buffer comprised of 4M urea, 50 mM $KH_2PO_4$, pH 7.0, 4 mM DTT. This is dialyzed against a 200-fold volume excess of buffer comprised of 50 mM Tris-Cl, pH 8.0, 1 mM DTT, 20% (v/v) glycerol overnight at 4° C. After dialysis, a four-fold molar excess of hemin (dissolved freshly in 0.1N KOH) is added to this protein solution. This is then dialyzed against 50 mM Tris-Cl, pH 8.0, 1 mM reduced glutathione (GSH), 100 μM oxidized glutathione (GSSG) overnight at 4° C. Finally, the sample was dialyzed against 10 mM sodium acetate, pH 6.0 overnight at 4° C. Modifications of this reconstitution procedure also have been demonstrated to be effective. One modification consists of dialysis of rLDM™ 6 against the Tris-Cl mixture in the presence of the glutathiones before hemin addition. This modified process is as follows:

(a) dialysis of a buffered solution comprising recombinant rLDM™ 6, 4M urea, 50 mM $KH_2PO_4$, DH 7.0, and 4 mM DTT, against a 200-fold volume excess of buffer comprising 50 mM Tris-Cl, pH 8.0, 1 mM reduced glutathione, 100 μM oxidized glutathione, overnight at 4° C.;

(b) adding about a 4-fold molar excess of hemin to the protein solution of (a); and (c) dialyzing the solution obtained in (b) against 10 mM sodium acetate at a pH of 6.0 overnight at 4° C.

Reconstitution is indicated by the presence of a Soret absorption band at 409 nm.

The above reconstitution protocol, with appropriate ranges of reagents and operating conditions, can be shown by the following steps:

(a) dialysis of a buffered solution comprising a ligninase protein, about 2M to about 8M urea at a pH of about 5 to about 9, and about 1 to about 10 mM of a reducing agent at a pH of about 5 to about 10, against about 0.5 to about 4 mM of the same reducing agent as above at a pH of about 5 to about 10, about 5 to about 30% (v/v) glycerol, for about 2 to about 24 hr at about 4° C. to about 37° C.;

(b) adding about a 1-fold to about a 10-fold molar excess of hemin to the protein solution of (a);

(c) dialyzing the solution of (b) against 0.1 to about 5 mM of a reduced sulfhydryl redox system, and about 10 to about 500 μM of an oxidized sulfhydryl redox system, at a pH of about 5 to about 10, for about 2 to about 24 hr, at about 4° C. to about 37° C.; and (d) dialyzing the solution obtained in (c) against an aqueous solution at a pH of about 4 to about 8, for about 2 to about 24 hr, at about 4° C. to about 37° C.

The above-described reconstitution procedure can be used for crude or relatively pure preparations of recombinant rLDM™ 6 expressed, for example, from cloned pLn105 or pLn106.

If a reconstitution procedure does not have resulting good specific veratryl alcohol oxidation activity there are several procedures, called reactivation procedures, which will result in rLDM™ 6 material with high specific activity. One such reactivation procedure is to dilute the initially reconstituted material to 0.1 mg/ml to 0.5 mg/ml rLDM™ 6 in 10–200 mM potassium phosphate or equivalent buffer, pH 5–7. Add 4-fold molar excess (over rLDM™ 6) of hemin. Incubate for 1–24 hr at 4° C. to 37° C. and repeat dialysis step in 10–200 mM potassium phosphate or equivalent buffer, pH 5–7 from 4–24 hr at 4° C. to 37° C. Alternatively, the initially reconstituted material, with no dilution, has a 4-fold molar excess (over rLDM™ 6) of hemin added followed by passage through a Sephadex G-50 column in 10–200 mM potassium phosphate or equivalent buffer, pH 5–7. The resulting eluant containing rLDM™ 6 has superior specific activity than the initial material.

Activity of Recombinant rLDM™ 6 Ligninase

Reconstituted recombinant ligninase rLDM™ 6 has been demonstrated active in lignin model compound assays and with lignin.

The lignin model compound assays that have been used are the veratryl alcohol oxidation (VAO) assay, the 1,2,4,5-tetramethoxybenzene (TMB) assay, and the adlerol assay. The VAO assay tests for oxidation of the $C_\alpha$ alcohol to an aldehyde. The TMB assay tests for demethoxylation. The products of the ligninase reaction, consuming 1 mole hydrogen peroxide per 1 mole of substrate, are 2 moles methanol and 2,5-methoxybenzoquinone. Reaction conditions are 20 mM sodium tartrate, pH 2.5, 64 μM hydrogen peroxide, and 1 mM 1,2,4,5-tetramethoxybenzene. The reaction is monitored at 450 nm, indicative of the yellow aryl cation radical intermediate species. The adlerol assay tests for cleavage of the $C_\alpha$–$C_\alpha$ bond and resulting oxidation to a $C_\alpha$ aldehyde. The reaction conditions and monitoring are identical to the VAO assay.

The lignin assay is carried out by measuring the rate of hydrogen peroxide consumption with time using a YSI model 25 Oxidase meter with a YSI 2510 Oxidase probe (Yellow Springs Instrument Co., Inc., Yellow Springs, OH). The reaction conditions are identical to the VAO assay but with 40 μM hydrogen peroxide and veratryl alcohol replaced by either milled wood lignin or kraft lignin at 20 to 250 μg/ml.

Chart 1 gives typical specific activities of reconstituted recombinant ligninase rLDM™ 6, expressed from clone pLn106 (see Example 13), in the VAO and TMB assays compared to specific activities of a pool of ligninases wherein P. chrysosporium LDM™ 6 is predominant. Specific activity with adlerol for rLDM™ 6 was comparable to that of P. chrysosporium LDM™ 6.

| Chart I<br>Ligninase Activity with Model compounds | | |
|---|---|---|
| | VAO<br>(units/mg)+ | TMB<br>(Au/mg)* |
| Reconstituted rLDM ™ 6 | 25.5 | 510 |
| P. chrysosporium LDM ™ 6 | 22.9 | 422 |

*TMB assay specific activities are expressed as increased absorption units per minute monitored at 450 nm per milligram rLDM ™ 6.
+VAO assay specific activities are expressed at International units (micromoles of veratrylaldehyde formed per minute) per milligram rLDM ™ 6.

The specific activities of reconstituted recombinant ligninase with lignins, demonstrated after a min addition, are 76.9 units/mg rLDM™ 6 on Indulin AT (kraft lignin) and 66.0 units/mg rLDM™ 6 on loblolly pine milled wood lignin. (A unit represents consumption of 1 nanomole of hydrogen peroxide per min).

Figure 4:
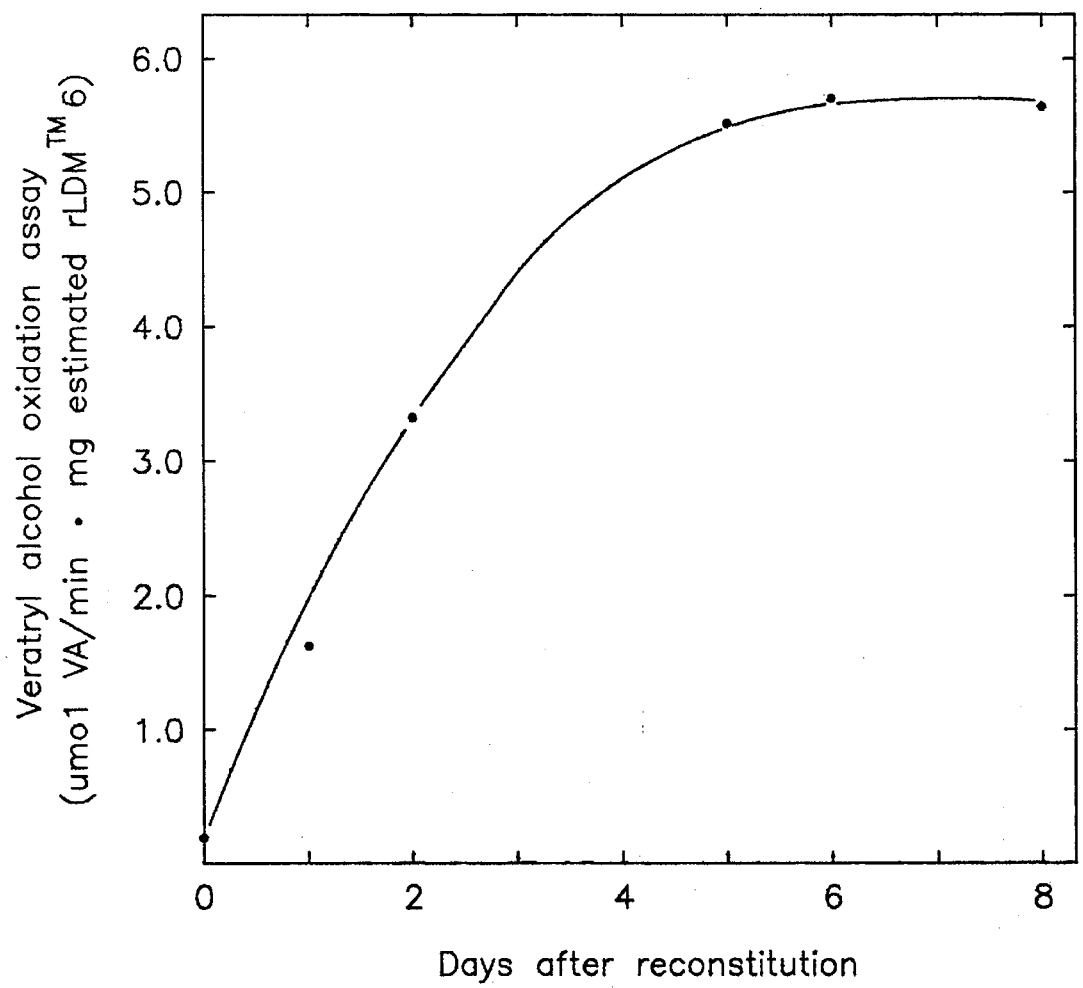
FIG. 4: Time Course of Activity Recovery-Reconstituted rLDM™ 6
Figure 5:
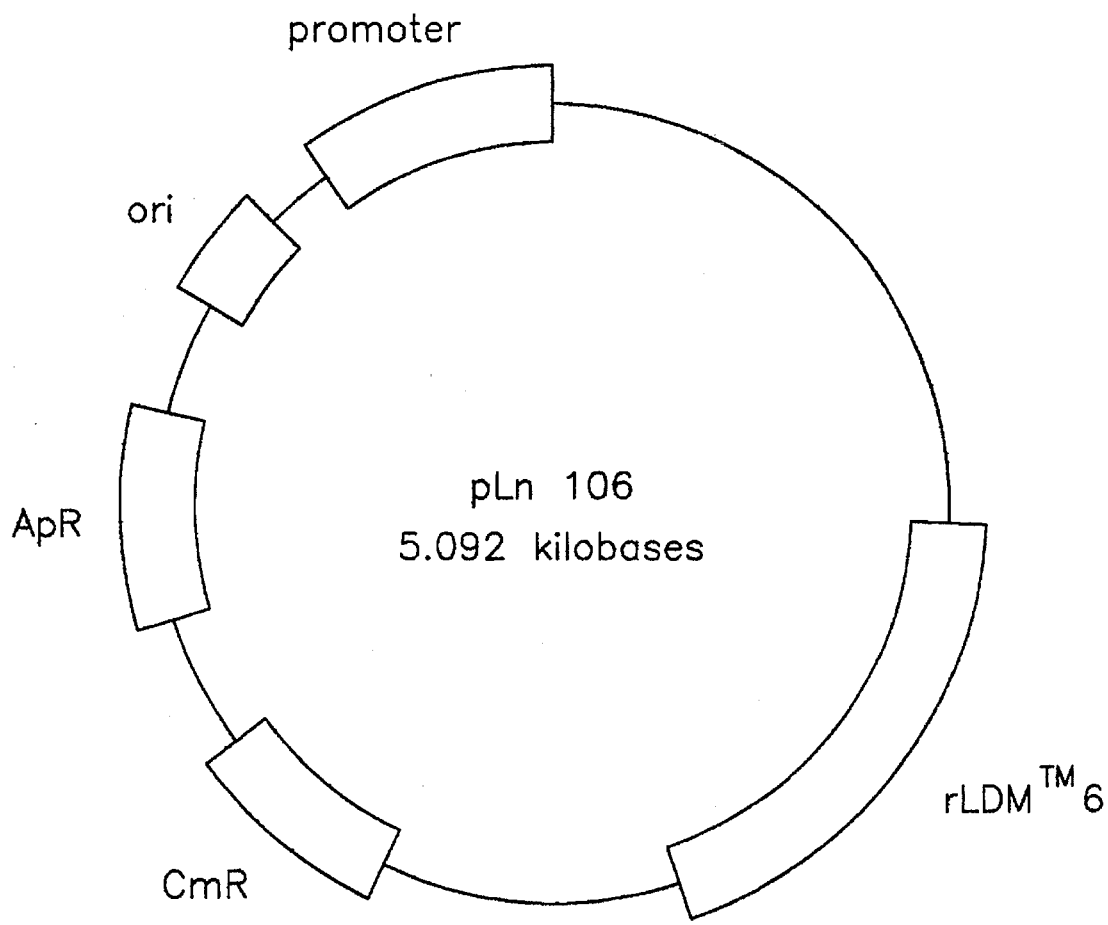
FIG. 5: Physical Map of pLn106

The last step in reconstitution is dialysis against 10 mM sodium acetate, pH 6.0. The activity of the reconstituted rLDM™ 6 increases upon storage after this last dialysis. FIG. 4 shows the increase in VAO activity with reconstituted rLDM™ 6 over an 8-day period with storage at 4° C. Day 0 represents the day the sample is taken out of the 10 mM sodium acetate, pH 6.0 dialysis. The VAO assays are run as previously described. The activity over the 8-day period has increased by 10-fold. After day 5 of storage, the activity does not further increase but remains very stable. P. chrysosporium ligninases do not show any increase in activity after dialysis and upon storage at 4° C.

This increase in activity with time of reconstituted rLDM™ 6 has been observed also in the assays with the lignins in the peroxide consumption assays and the TMB assay. An increase in activity after isolation has not been observed with the native P. chrysosporium material.

The activity of 7-day stored rLDM™ 6 calculated from peroxide consumption, is 76.9 unit/mg rLDM™ 6, where a unit represents consumption of 1 nanomole hydrogen peroxide per minute versus 39.1 unit/mg rLDM™ 6 of 6-day stored enzyme. The increase in activity may be temperature dependent. Chart 2 shows the data from an experiment done with the same reconstituted rLDM™ 6 material used and represented in FIG. 4. Reconstitution of the desired protein products of the other foregoing examples, and the following Example 13, results in ligninase protein having a similar VAO activity, except that the protein from pBSR3 (Example 6a) exhibited a lower order of such activity.

The terms "ligninase" protein, "ligninolytic" and the like, as used herein, mean a protein having ligninase activity, or a protein capable of having such activity when reconstituted with protoheme IX.

The terms "heme," "hemin" or "protoheme IX," as used herein, denote the oxidized $FE^{+3}$ form of protoheme IX.

The term "apoprotein" as used with reference to ligninase protein denotes protein which has not been reconstituted with heme.

Chart 2
Increased Activity of rLDM ™ 6--
Temperature Dependent

| Day | Storage Temperature | VAO activity Units/mg rLDM ™ 6 (all assays at 37°C.) |
| --- | --- | --- |
| 5 | starting material | 5.55 |
| 6 | 4° C. | 5.70 |
|  |  | 5.65 |
|  | 23° C. | 7.25 |
|  |  | 7.05 |

The duplicates left at room temperature increased in activity over the duplicates left at 4° C. by 26%.

EXAMPLE 13—Construction and Expression of Recombinant rLDM™ 6 from *S. cerevisiae*

Plasmid pLn1001 was constructed by ligation of the nucleotide sequences of rLDM™ 6 initiating with position 91 given in Table 1 and ending with position 1172, with the approximately 1,000 bp EcoRI-HaeIII fragment of the plasmid pTPIC-10 (triose phosphase isomerase transcription terminator) (Alber, T. and Kawasaki, G. 82) Jour. of Molec. and Applied Gen. 1:419–432). This approximately 2172 bp fragment was ligated with the approximately 700 bp EcoRI-EcoRV fragment from plasmid pTPIC-10 and the 56 bp oligonucleotide having the sequence

CTCTTTTGCAAGCTTTCCTTTTCCTTTTGGC
TGGTTTTGCAGCCAAAATATCTGCA.

The resulting plasmid, pLn1001 (NRRL Y-18163), was transformed into the host *S. cerevisiae* DBY747 (University of California, Berkeley, Yeast Genetic Stock Center) grown in minimal medium supplemented with leucine, uracil, tryptophan, methionine, casamino acids (Difco, Detroit, Mich.) and glucose and incubated 18 hr at 30° C. with vigorous shaking. Alternatively, the host can be grown in synthetic medium containing 0.67% yeast nitrogen base, 2% glucose and 0.5% casamino acids (Difco). Cells were harvested and lysed by bead milling. From the insoluble cell pellet rLDM™ 6 protein, of apparent molecular size 41 kd, was detected by immunological reaction with polyclonal antibodies made to *P. chrysosporium* LDM™ 6.

The nucleotide sequence obtained from an rLDM™ 6 clone also can be prepared by a "gene machine" by procedures well known in the art. This is possible because of the disclosure of the nucleotide sequence.

rLDM™ 6 can be chemically synthesized by solid phase peptide synthetic techniques such as BOC and FMOC (Merrifield, R. B. [1963] J. Amer. Chem. Soc. 85:2149; Chang, C. and Meienhofer, J. [1978] Int. J. Peptide Protein Res. 11:246). Synthesis is from the C-terminal end and as long as any additional amino acids are added to the amino acid to the amino terminal side of the proteolytic product with rLDM™ 6 activity, these additional amino acids can be removed by cleavage with these proteases to give a protein with rLDM™ 6 activity.

The method for chemically synthesizing peptides is described in Merrifield, R. B. (1963) J. Amer. Chem. Soc. 85:2149; Chang, C. and Meienhofer, J. (1978) Int. J. Peptide Protein Res. 11:246; and Bodanzsky, M. (1984) Principles of Peptide Synthesis, Springer-Verlag.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
| --- | --- | --- | --- |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose-sequence corresponds to the mRNA sequence, with thymine substituted for uracil. The letters stand for the purine or pyrimidine bases forming the deoxynucleotide sequence.

A=adenine

G=guanine

C=cytosine

T=thymine

X=T or C if Y is A or G

X=C if Y is C or T

Y=A, G, C or T if X is C

Y=A or G if X is T

W=C or A if Z is A or G

W=C if Z is C or T

Z=A, G, C or T if W is C

Z=A or G if W is A

QR=Tc if S is A, G, C or T; alternatively,

QR=AG if S is T or C

J=A or G

K=T or C

L=A, T, C or G

M=A, C or T

The above shows that the novel amino acid sequences of the subject invention can be prepared by nucleotide sequences other than those disclosed herein. Functionally equivalent nucleotide sequences encoding the novel amino acid sequences of these proteins, or fragments thereof having ligninase activity, can be prepared by known synthetic procedures. Accordingly, the subject invention includes such functionally equivalent nucleotide sequences.

In addition it has been shown that proteins of identified structure and function may be constructed by changing the amino acid sequence if such changes do not alter the protein secondary structure (Kaiser, E. T. and Kezdy, F. J. [1984] Science 223:249–255). Thus the subject invention includes routants of the amino acid sequences depicted herein which do not alter the protein secondary structure, or if the structure is altered, the biological activity is retained to some degree.

As shown above, it is well within the skill of those in the genetic engineering art to use the nucleotide sequences encoding rLDM™ 6 activity of the subject invention to produce proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare proteins of the subject invention by microbial means or mammalian tissue culture technology.

The gene for rLDM™ 6 can be isolated from genomic DNA, a so-called genomic clone, by using partial sequences from the cDNA of rLDM™ 6 as a probe. These techniques are well known in the art; see Maniatis, T., Fritsch, E. F. and Sambrook, J. *Molecular Cloning: A Laboratory Manual*, Cold Spring Harbor Laboratory, N.Y., 1982. The genomic clone thus obtained can be inserted into suitable vectors for various hosts.

TABLE 1

Nucleotide Sequence and Deduced Amino Acid Sequence of rLDM™6

GAA TTC CGA GAG AGA TAG CTG CGA AGA GCT GCT ATC TCT CTC

GCT CTC TTG CTC TCG GCT GCG AAC GCG GCT GCG GTG ATC GAG

Position 91
Position 88

AAG CGC GCC ACC TGT TCC AAC GGC AAG ACC GTC GGC GAT GCG
ARG ALA THR CYS SER ASN GLY LYS THR VAL GLY ASP ALA
(−1) (1)

EcoRV
↓
TCG TGC TGC GCT TGG TTC GAC GTC CTG GAT GAT ATC CAG CAG
SER GYS CYS ALA TRP PHE ASP VAL LEU ASP ASP ILE GLN GLN

FnuHI      HaeII
↓      ↓
AAC CTG TTC CAC GGC GGC CAG TGC GGC GCT GAG GCG CAC GAG
ASN LEU PHE HIS GLY GLY GLN CYS GLY ALA GLU ALA HIS GLU

TCG ATT CGT CTC GTC TTC CAC GAC TCC ATC GCA ATT TCG CCC
SER ILE ARG LEU VAL PHE HIS ASP SER ILE ALA ILE SER PRO

GCC ATG GAG GCA CAG GGC AAG TTC GGC GGC GGT GGT GCT GAC
ALA MET GLU ALA GLN GLY LYS PHE GLY GLY GLY GLY ALA ASP

GGC TCC ATC ATG ATC TTC GAC GAT ATC GAG ACT GCG TTC CAC
GLY SER ILE MET ILE PHE ASP ASP ILE GLU THR ALA PHE HIS

CCT AAC ATC GGT CTC GAC GAG ATC GTC AAG CTC CAG AAG CCA
PRO ASN ILE GLY LEU ASP GLU ILE VAL LYS LEU GLN LYS PRO

TTC GTT CAG AAG CAC GGT GTC ACC CCT GGT GAC TTC ATC GCC
PHE VAL GLN LYS HIS GLY VAL THR PRO GLY ASP PHE ILE ALA

TTC GCT GGT GCT GTC GCG CTC AGC AAC TGC CCT GGT GCC CCG
PHE ALA GLY ALA VAL ALA LEU SER ASN CYS PRO GLY ALA PRO

CAG ATG AAC TTC TTC ACT GGT CGT GCA CCT GCT ACC CAG CCC
GLN MET ASN PHE PHE THR GLY ARG ALA PRO ALA THR GLN PRO

HaeIII
↓
GCT CCT GAT GGC CTT GTC CCC GAG CCC TTC CAC ACT GTC GAC
ALA PRO ASP GLY LEU VAL PRO GLU PRO PHE HIS THR VAL ASP

CAA ATC ATC AAC CGT GTC AAC GAC GCA GGC GAG TTC GAT GAG
GLN ILE ILE ASN ARG VAL ASN ASP ALA GLY GLU PHE ASP GLU

CTC GAG CTT GTC TGG ATG CTC TCC GCG CAC TCC GTC GCA GCG
LEU GLU LEU VAL TRP MET LEU SER ALA HIS SER VAL ALA ALA

GTG AAC GAC GTC GAC CCG ACC GTC CAG GGT CTG CCC TTT GAC
VAL ASN ASP VAL ASP PRO THR VAL GLN GLY LEU PRO PHE ASP

TCG ACC CCC GGA ATC TTC GAC TCC CAG TTC TTC GTC GAG ACT
SER THR PRO GLY ILE PHE ASP SER GLN PHE PHE VAL GLU THR

CAG CTT CGT GGT ACC GCC TTC CCC GGC TCT GGC GGC AAC CAA
GLN LEU ARG GLY THR ALA PHE PRO GLY SER GLY GLY ASN GLN

GGC GAG GTC GAG TCG CCG CTC CCT GGC GAA ATT CGC ATC CAG
GLY GLU VAL GLU SER PRO LEU PRO GLY GLU ILE ARG ILE GLN

TCC GAC CAC ACT ATC GCC CGC GAC TCA CGC ACG GCG TGT GAA
SER ASP HIS THR ILE ALA ARG ASP SER ARG THR ALA CYS GLU

TABLE 1-continued

Nucleotide Sequence and Deduced Amino Acid Sequence of rLDM™6

TGG CAG TCC TTC GTC AAC AAC CAG TCC AAG CTC GTC GAT GAC
TRP GLN SER PHE VAL ASN ASN GLN SER LYS LEU VAL ASP ASP

TTC CAA TTC ATT TTC CTC GCC CTC ACC CAG CTC GGC CAG GAC
PHE GLN PHE ILE PHE LEU ALA LEU THR GLN LEU GLY GLN ASP

CCG AAC GCG ATG ACC GAC TGC TCG GAT GTT ATC CCG CAG TCC
PRO ASN ALA MET THR ASP CYS SER ASP VAL ILE PRO GLN SER

AAG CCC ATC CCT GGC AAC CTC CCA TTC TCG TTC TTC CCC GCT
LYS PRO ILE PRO GLY ASN LEU PRO PHE SER PHE PHE PRO ALA

GGC AAG ACC ATC AAA GAC GTT GAG CAG GCG TGT GCG GAG ACC
GLY LYS THR ILE LYS ASP VAL GLU GLN ALA CYS ALA GLU THR

CCC TTC CCG ACT CTC ACC ACT CTC CCG GGC CCC GAG ACG TCC
PRO PHE PRO THR LEU THR THR LEU PRO GLY PRO GLU THR SER

GTC CAG CGC ATC CCT CCG CCT CCG GGT GCT TAG ATG ATT CCA
VAL GLN ARG ILE PRO PRO PRO PRO GLY ALA *** MET ILE PRO
                                         (344)

HaeIII
                                              ↓
TAC AGA ATA CGC CTC GAA CCG ACT GTA ACG GTG GCC GGC TAA
TYR ARG ILE ARG LEU GLU PRO THR VAL THR VAL ALA GLY
                                                 (361)
CTC GTG ACG GAA CTT CGG CTT TAC TAG ATT TCA TCC ATT GTA

TCT CTG CAT CTG ACT ACG AAT CTT ATT CGT CTA CTC TCT TAA

AAA AAA AAA AAC CGG AAT

In Table 1 the DNA nucleotides of the coding sequence have been linearly grouped in triplets or codons consistent with the amino acid protein sequence for which the DNA encodes. The nucleotides have been numbered at various locations in Table 1 either above the line in which they appear or by the use of arrows. Table 1 also sets forth the amino acid protein sequence encoded for by the nucleotide sequence, and amino acids (and stops) in such protein sequence have been numbered in parenthesis below the line in which they appear (positive numbering beginning with the first amino acid of the ascertained mature sequence). Nucleotide triplets (codons) representing stop signals have been assigned a triple asterisk in the predicted amino acid sequence, it being understood that the codon TAG is not an efficient terminator in suppressing hosts; thus the protein is extended to the next TAA codon. In contrast, in suppressor-free hosts the protein will terminate at the TAG codon. The particular suppressor strain in which the protein is expressed will determine which amino acid is incorporated at the amber stop codon designated by the triple asterisk.

It has been ascertained that part of the nucleotide sequence prior to the 1-position Ala is an artifact or otherwise unrelated to the presumed signal sequence encoded by the native mRNA.

We claim:

1. An isolated DNA molecule coding for ligninase protein comprising the following amino acid sequence:

|     |     | ALA | THR | CYS | SER | ASN |
| --- | --- | --- | --- | --- | --- | --- |
| GLY | LYS | THR | VAL | GLY | ASP | ALA |
| SER | CYS | CYS | ALA | TRP | PHE | ASP |
| VAL | LEU | ASP | ASP | ILE | GLN | GLN |
| ASN | LEU | PHE | HIS | GLY | GLY | GLN |
| CYS | GLY | ALA | GLU | ALA | HIS | GLU |
| SER | ILE | ARG | LEU | VAL | PHE | HIS |
| ASP | SER | ILE | ALA | ILE | SER | PRO |
| ALA | MET | GLU | ALA | GLN | GLY | LYS |
| PHE | GLY | GLY | GLY | GLY | ALA | ASP |
| GLY | SER | ILE | MET | ILE | PHE | ASP |
| ASP | ILE | GLU | THR | ALA | PHE | HIS |
| PRO | ASN | ILE | GLY | LEU | ASP | GLU |
| ILE | VAL | LYS | LEU | GLN | LYS | PRO |
| PHE | VAL | GLN | LYS | HIS | GLY | VAL |
| THR | PRO | GLY | ASP | PHE | ILE | ALA |
| PHE | ALA | GLY | ALA | VAL | ALA | LEU |
| SER | ASN | CYS | PRO | GLY | ALA | PRO |
| GLN | MET | ASN | PHE | PHE | THR | GLY |
| ARG | ALA | PRO | ALA | THR | GLN | PRO |
| ALA | PRO | ASP | GLY | LEU | VAL | PRO |
| GLU | PRO | PHE | HIS | THR | VAL | ASP |
| GLN | ILE | ILE | ASN | ARG | VAL | ASN |
| ASP | ALA | GLY | GLU | PHE | ASP | GLU |
| LEU | GLU | LEU | VAL | TRP | MET | LEU |
| SER | ALA | HIS | SER | VAL | ALA | ALA |
| VAL | ASN | ASP | VAL | ASP | PRO | THR |
| VAL | GLN | GLY | LEU | PRO | PHE | ASP |
| SER | THR | PRO | GLY | ILE | PHE | ASP |
| SER | GLN | PHE | PHE | VAL | GLU | THR |
| GLN | LEU | ARG | GLY | THR | ALA | PHE |
| PRO | GLY | SER | GLY | GLY | ASN | GLN |
| GLY | GLU | VAL | GLU | SER | PRO | LEU |
| PRO | GLY | GLU | ILE | ARG | ILE | GLN |
| SER | ASP | HIS | THR | ILE | ALA | ARG |
| ASP | SER | ARG | THR | ALA | CYS | GLU |
| TRP | GLN | SER | PHE | VAL | ASN | ASN |
| GLN | SER | LYS | LEU | VAL | ASP | ASP |
| PHE | GLN | PHE | ILE | PHE | LEU | ALA |
| LEU | THR | GLN | LEU | GLY | GLN | ASP |
| PRO | ASN | ALA | MET | THR | ASP | CYS |
| SER | ASP | VAL | ILE | PRO | GLN | SER |
| LYS | PRO | ILE | PRO | GLY | ASN | LEU |

-continued

| | | | | | | |
|---|---|---|---|---|---|---|
| PRO | PHE | SER | PHE | PHE | PRO | ALA |
| GLY | LYS | THR | ILE | LYS | ASP | VAL |
| GLU | GLN | ALA | CYS | ALA | GLU | THR |
| PRO | PHE | PRO | THR | LEU | THR | THR |
| LEU | PRO | GLY | PRO | GLU | THR | SER |
| VAL | GLN | ARG | ILE | PRO | PRO | PRO |
| PRO | GLY | ALA. | | | | |

2. The DNA molecule of claim 1 in which the N-terminal codon coding for Ala is preceded by ATG coding for Met.

3. An isolated DNA molecule selected from the group consisting of
   a) a DNA molecule coding for a ligninase protein comprising the nucleotide sequence set forth in Table I; and
   b) a DNA molecule which hybridizes to the DNA molecule in a) under stringent hybridization conditions and codes on expression for the ligninase protein comprising the amino acid sequence according to claim 1.

4. An isolated DNA molecule coding for ligninase protein comprising the following amino acid sequence:

5. The DNA molecule of claim 4 in which the N-terminal codon coding for Ala is preceded by ATG coding for Met.

6. A process for preparing the amino acid sequence encoded by The DNA of claim 4 which comprises culturing a prokaryotic or eukaryotic host containing a recombinant DNA transfer vector encoding said DNA and harvesting said amino acid sequence from the host.

7. A process for preparing the amino acid sequence encoded by the DNA of claim 4 with Met preceding the initial Ala which comprises culturing a prokaryotic or eukaryotic host containing a recombinant DNA transfer vector encoding said DNA and harvesting said amino acid sequence from the host.

8. A transfer vector comprising a gene coding for a ligninolytic protein, said gene comprising the following amino acid sequence:

| | | | | | | | | | | | | | |
|---|---|---|---|---|---|---|---|---|---|---|---|---|---|
| | | ALA | THR | CYS | SER | ASN | GLY | LYS | THR | VAL | GLY | ASP | ALA |
| SER | CYS | CYS | ALA | TRP | PHE | ASP | VAL | LEU | ASP | ASP | ILE | GLN | GLN |
| ASN | LEU | PHE | HIS | GLY | GLY | GLN | CYS | GLY | ALA | GLU | ALA | HIS | GLU |
| SER | ILE | ARG | LEU | VAL | PHE | HIS | ASP | SER | ILE | ALA | ILE | SER | PRO |
| ALA | MET | GLU | ALA | GLN | GLY | LYS | PHE | GLY | GLY | GLY | GLY | ALA | ASP |
| GLY | SER | ILE | MET | ILE | PHE | ASP | ASP | ILE | GLU | THR | ALA | PHE | HIS |
| PRO | ASN | ILE | GLY | LEU | ASP | GLU | ILE | VAL | LYS | LEU | GLN | LYS | PRO |
| PHE | VAL | GLN | LYS | HIS | GLY | VAL | THR | PRO | GLY | ASP | PHE | ILE | ALA |
| PHE | ALA | GLY | ALA | VAL | ALA | LEU | SER | ASN | CYS | PRO | GLY | ALA | PRO |
| GLN | MET | ASN | PHE | PHE | THR | GLY | ARG | ALA | PRO | ALA | THR | GLN | PRO |
| ALA | PRO | ASP | GLY | LEU | VAL | PRO | GLU | PRO | PHE | HIS | THR | VAL | ASP |
| GLN | ILE | ILE | ASN | ARG | VAL | ASN | ASP | ALA | GLY | GLU | PHE | ASP | GLU |
| LEU | GLU | LEU | VAL | TRP | MET | LEU | SER | ALA | HIS | SER | VAL | ALA | ALA |
| VAL | ASN | ASP | VAL | ASP | PRO | THR | VAL | GLN | GLY | LEU | PRO | PHE | ASP |
| SER | THR | PRO | GLY | ILE | PHE | ASP | SER | GLN | PHE | PHE | VAL | GLU | THR |
| GLN | LEU | ARG | GLY | THR | ALA | PHE | PRO | GLY | SER | GLY | GLY | ASN | GLN |
| GLY | GLU | VAL | GLU | SER | PRO | LEU | PRO | GLY | GLU | ILE | ARG | ILE | GLN |
| SER | ASP | HIS | THR | ILE | ALA | ARG | ASP | SER | ARG | THR | ALA | CYS | GLU |
| TRP | GLN | SER | PHE | VAL | ASN | ASN | GLN | SER | LYS | LEU | VAL | ASP | ASP |
| PHE | GLN | PHE | ILE | PHE | LEU | ALA | LEU | THR | GLN | LEU | GLY | GLN | ASP |
| PRO | ASN | ALA | MET | THR | ASP | CYS | SER | ASP | VAL | ILE | PRO | GLN | SER |
| LYS | PRO | ILE | PRO | GLY | ASN | LEU | PRO | PHE | SER | PHE | PHE | PRO | ALA |
| GLY | LYS | THR | ILE | LYS | ASP | VAL | GLU | GLN | ALA | CYS | ALA | GLU | THR |
| PRO | PHE | PRO | THR | LEU | THR | THR | LEU | PRO | GLY | PRO | GLU | THR | SER |
| VAL | GLN | ARG | ILE | PRO | PRO | PRO | GLY | ALA | *** | MET | ILE | PRO |
| TYR | ARG | ILE | ARG | LEU | GLU | PRO | THR | VAL | THR | VAL | ALA | GLY. |

| | | | | | | | | | | | | | |
|---|---|---|---|---|---|---|---|---|---|---|---|---|---|
| | | ALA | THR | CYS | SER | ASN | GLY | LYS | THR | VAL | GLY | ASP | ALA |
| SER | CYS | CYS | ALA | TRP | PHE | ASP | VAL | LEU | ASP | ASP | ILE | GLN | GLN |
| ASN | LEU | PHE | HIS | GLY | GLY | GLN | CYS | GLY | ALA | GLU | ALA | HIS | GLU |
| SER | ILE | ARG | LEU | VAL | PHE | HIS | ASP | SER | ILE | ALA | ILE | SER | PRO |
| ALA | MET | GLU | ALA | GLN | GLY | LYS | PHE | GLY | GLY | GLY | GLY | ALA | ASP |
| GLY | SER | ILE | MET | ILE | PHE | ASP | ASP | ILE | GLU | THR | ALA | PHE | HIS |
| PRO | ASN | ILE | GLY | LEU | ASP | GLU | ILE | VAL | LYS | LEU | GLN | LYS | PRO |
| PHE | VAL | GLN | LYS | HIS | GLY | VAL | THR | PRO | GLY | ASP | PHE | ILE | ALA |
| PHE | ALA | GLY | ALA | VAL | ALA | LEU | SER | ASN | CYS | PRO | GLY | ALA | PRO |
| GLN | MET | ASN | PHE | PHE | THR | GLY | ARG | ALA | PRO | ALA | THR | GLN | PRO |
| ALA | PRO | ASP | GLY | LEU | VAL | PRO | GLU | PRO | PHE | HIS | THR | VAL | ASP |
| GLN | ILE | ILE | ASN | ARG | VAL | ASN | ASP | ALA | GLY | GLU | PHE | ASP | GLU |
| LEU | GLU | LEU | VAL | TRP | MET | LEU | SER | ALA | HIS | SER | VAL | ALA | ALA |
| VAL | ASN | ASP | VAL | ASP | PRO | THR | VAL | GLN | GLY | LEU | PRO | PHE | ASP |
| SER | THR | PRO | GLY | ILE | PHE | ASP | SER | GLN | PHE | PHE | VAL | GLU | THR |
| GLN | LEU | ARG | GLY | THR | ALA | PHE | PRO | GLY | SER | GLY | GLY | ASN | GLN |
| GLY | GLU | VAL | GLU | SER | PRO | LEU | PRO | GLY | GLU | ILE | ARG | ILE | GLN |
| SER | ASP | HIS | THR | ILE | ALA | ARG | ASP | SER | ARG | THR | ALA | CYS | GLU |
| TRP | GLN | SER | PHE | VAL | ASN | ASN | GLN | SER | LYS | LEU | VAL | ASP | ASP |

| | | | | | | | | | | | | | |
|---|---|---|---|---|---|---|---|---|---|---|---|---|---|
| PHE | GLN | PHE | ILE | PHE | LEU | ALA | LEU | THR | GLN | LEU | GLY | GLN | ASP |
| PRO | ASN | ALA | MET | THR | ASP | CYS | SER | ASP | VAL | ILE | PRO | GLN | SER |
| LYS | PRO | ILE | PRO | GLY | ASN | LEU | PRO | PHE | SER | PHE | PHE | PRO | ALA |
| GLY | LYS | THR | ILE | LYS | ASP | VAL | GLU | GLN | ALA | CYS | ALA | GLU | THR |
| PRO | PHE | PRO | THR | LEU | THR | THR | LEU | PRO | GLY | PRO | GLU | THR | SER |
| VAL | GLN | ARG | ILE | PRO | PRO | PRO | PRO | GLY | ALA. | | | | |

9. A transfer vector, according to claim 8, wherein the gene codes for an amino acid sequence in which the N-terminal Ala is preceded by Met.

10. A transfer vector comprising a gene coding for a ligninolytic protein, said gene comprising the following amino acid sequence:

| | | | | | | | | | | | | | |
|---|---|---|---|---|---|---|---|---|---|---|---|---|---|
| | ALA | THR | CYS | SER | ASN | GLY | LYS | THR | VAL | GLY | ASP | ALA | |
| SER | CYS | CYS | ALA | TRP | PHE | ASP | VAL | LEU | ASP | ASP | ILE | GLN | GLN |
| ASN | LEU | PHE | HIS | GLY | GLY | GLN | CYS | GLY | ALA | GLU | ALA | HIS | GLU |
| SER | ILE | ARG | LEU | VAL | PHE | HIS | ASP | SER | ILE | ALA | ILE | SER | PRO |
| ALA | MET | GLU | ALA | GLN | GLY | LYS | PHE | GLY | GLY | GLY | GLY | ALA | ASP |
| GLY | SER | ILE | MET | ILE | PHE | ASP | ASP | ILE | GLU | THR | ALA | PHE | HIS |
| PRO | ASN | ILE | GLY | LEU | ASP | GLU | ILE | VAL | LYS | LEU | GLN | LYS | PRO |
| PHE | VAL | GLN | LYS | HIS | GLY | VAL | THR | PRO | GLY | ASP | PHE | ILE | ALA |
| PHE | ALA | GLY | ALA | VAL | ALA | LEU | SER | ASN | CYS | PRO | GLY | ALA | PRO |
| GLN | MET | ASN | PHE | PHE | THR | GLY | ARG | ALA | PRO | ALA | THR | GLN | PRO |
| ALA | PRO | ASP | GLY | LEU | VAL | PRO | GLU | PRO | PHE | HIS | THR | VAL | ASP |
| GLN | ILE | ILE | ASN | ARG | VAL | ASN | ASP | ALA | GLY | GLU | PHE | ASP | GLU |
| LEU | GLU | LEU | VAL | TRP | MET | LEU | SER | ALA | HIS | SER | VAL | ALA | ALA |
| VAL | ASN | ASP | VAL | ASP | PRO | THR | VAL | GLN | GLY | LEU | PRO | PHE | ASP |
| SER | THR | PRO | GLY | ILE | PHE | ASP | SER | GLN | PHE | PHE | VAL | GLU | THR |
| GLN | LEU | ARG | GLY | THR | ALA | PHE | PRO | GLY | SER | GLY | GLY | ASN | GLN |
| GLY | GLU | VAL | GLU | SER | PRO | LEU | PRO | GLY | GLU | ILE | ARG | ILE | GLN |
| SER | ASP | HIS | THR | ILE | ALA | ARG | ASP | SER | ARG | THR | ALA | CYS | GLU |
| TRP | GLN | SER | PHE | VAL | ASN | ASN | GLN | SER | LYS | LEU | VAL | ASP | ASP |
| PHE | GLN | PHE | ILE | PHE | LEU | ALA | LEU | THR | GLN | LEU | GLY | GLN | ASP |
| PRO | ASN | ALA | MET | THR | ASP | CYS | SER | ASP | VAL | ILE | PRO | GLN | SER |
| LYS | PRO | ILE | PRO | GLY | ASN | LEU | PRO | PHE | SER | PHE | PHE | PRO | ALA |
| GLY | LYS | THR | ILE | LYS | ASP | VAL | GLU | GLN | ALA | CYS | ALA | GLU | THR |
| PRO | PHE | PRO | THR | LEU | THR | THR | LEU | PRO | GLY | PRO | GLU | THR | SER |
| VAL | GLN | ARG | ILE | PRO | PRO | PRO | PRO | GLY | ALA | *** | MET | ILE | PRO |
| TYR | ARG | ILE | ARG | LEU | GLU | PRO | THR | VAL | THR | VAL | ALA | GLY. | |

11. A transfer vector, according to claim 10, wherein the gene codes for an amino acid sequence in which the N-terminal Ala is preceded by Met.

12. A transfer vector, in accord with claims 8, 9, 10, or 11, in which the gene is regulated by control sequences of the genomic DNA sequence of native origin.

13. The DNA transfer vector of claims 8, 9, 10, or 11, contained in a prokaryotic or eukaryotic host.

14. A DNA transfer vector in accord with claim 12, contained in a prokaryotic or eukaryotic host.

15. The DNA transfer vector of claim 13 contained in a yeast.

16. A plasmid selected from pBSR3, pLn105, pLn106, or pLn1001.

* * * * *